United States Patent [19]

Prahl et al.

[11] Patent Number: 4,997,449
[45] Date of Patent: Mar. 5, 1991

[54] ARTIFICIAL KNEE JOINT

[75] Inventors: Gregor M. Prahl, Rullstorf; Reinhold Schneider, Bardowick, both of Fed. Rep. of Germany

[73] Assignee: Ipos GmbH & Co., KG., Luneburg, Fed. Rep. of Germany

[21] Appl. No.: 249,348

[22] Filed: Sep. 23, 1988

[30] Foreign Application Priority Data

Aug. 3, 1988 [DE] Fed. Rep. of Germany ... 8809910[U]

[51] Int. Cl.$^5$ .............................................. A61F 2/64
[52] U.S. Cl. ........................................ 623/44; 623/46
[58] Field of Search .................. 623/18, 49, 43, 44, 623/39, 45, 46

[56] References Cited

U.S. PATENT DOCUMENTS

| | | | |
|---|---|---|---|
| 2,645,779 | 7/1953 | Barghausen | 623/45 |
| 3,723,997 | 4/1973 | Kolman | 623/46 X |
| 4,064,569 | 12/1977 | Campbell | 623/38 |
| 4,135,254 | 1/1979 | Weber et al. | 623/46 |
| 4,206,519 | 6/1980 | Blatchford et al. | 623/44 |
| 4,456,003 | 6/1984 | Allard | 623/44 |
| 4,549,318 | 10/1985 | Takahama | 623/44 |
| 4,685,926 | 8/1987 | Haupt | 623/43 |

FOREIGN PATENT DOCUMENTS 2023040 8/1971 Fed. Rep. of Germany ........ 623/43

*Primary Examiner*—Alan Cannon
*Assistant Examiner*—David H. Willse

[57] ABSTRACT

An artificial knee joint (10) with a clamping member (13) is provided with a peg (11) for attachment to a thigh shaft (12). The clamping member is pivotable against a braking member or barrel (19) located inside the knee joint housing when a vertical load (44) is applied to the knee joint to arrest the swiveling movement a leg part (26). The leg part accommodates the lower leg tube of a leg prosthesis as well as a traction strap (36) impelling the knee joint back into the straightened position. By this means an uncontrolled buckling of the artificial knee joint is prevented in the event that a prosthesis wearer stumbles.

11 Claims, 5 Drawing Sheets

ARTIFICIAL KNEE JOINT

BACKGROUND OF THE INVENTION

The present invention relates to an artificial knee joint with a clamping member including a peg for attachment onto a thigh shaft, a lower leg part accommodating a leg prosthesis and a joint casing interconnecting the clamping member and the leg part for pivotal movement of the joint. The clamping member swivels relative to the joint casing and presses against a braking member located inside the joint casing when a vertical load is applied to the knee joint. When the clamping member presses against the braking member, pivotal movement of the joint and the lower leg part with the prosthesis is arrested. A traction strap connected between the lower leg part and the casing tends to return the joint or impel the knee joint back into the stretched or straightened position from a bent position.

The fundamental objective in a prosthesis is to bring about the natural coordinated movements of the substituted member of the body as closely as possible. In the case of artificial legs there arises especially the problem that the load braking systems known according to the state of the art are incapable of optimally doing justice to the safety requirements of the elderly. Due to friction contact processes, locomotion processes such as develop during the natural walk sequence are interfered with in a non-physiological manner with the consequence that these load braking systems lead to the wearer of the prosthesis having a fall.

Over and above that, in the knee joint constructions according to the state of the art, the reduction in size of the joints has resulted in dimensions in which braking forces that are capable of holding a knee in a bent position, results in an overstraining of the joint construction and of the material. Not infrequently this causes substantial wear of the friction surfaces, noisy working knee joints and an increased need for servicing.

It is accordingly an object of the present invention to improve the knee joint referred to above so that an uncontrolled flection or pivoting of the joint under a vertical load is contained during bending movement, while all extension or straightening movements of the knee joint remain freely executable. The automatic engagement of a brake lining is made possible hereby. The construction of the knee joint in particular has to be simple and must operate with minimal wear.

SUMMARY OF THE INVENTION

In the knee joint referred to in the beginning, this technical problem is solved in that the knee joint casing, in the rear region, is provided with an essentially cylindrical barrel which is swivelingly supported with a horizontally arranged rotary axis. The ends of the barrel are rigidly secured against rotation within the fork arms of the lower leg part intended to accommodate the lower leg tube. The casing within the front region has a forked mounting, within which the clamping member is swivelably supported on an axis for bending and a stretching or straightening movement. When a vertical load is applied, the clamping member comes to bear against the barrel in a manner which prevents and blocks a flection (bending movement). Advantageously all extension movements, i.e. movements of the knee joint in the forward direction, are possible even if an involuntary vertical load does occur. The clamping member and the barrel act like a freewheel device which blocks the bending movement only when a vertical load occurs and thereby prevents a (further) buckling. Particularly the entire dynamic locomotion process of the patient is not interfered with since the forward movement of the entire prosthesis body is capable of making itself felt freely without any limitation of the extension movement of the artificial limb when a vertical load occurs. When the extension movement is able to take place unimpeded, a fall can very largely be prevented. Despite the comparatively simple construction of the knee joint, it offers a minimized attrition due to wear.

Preferably, two possibilities present themselves for a rotation-secured mounting of the barrel onto the fork arms of the lower leg part intended to accommodate the lower leg tube: In the first one, the barrel may be provided on its ends with, in each case, at least one, preferably three, tapped blind holes, or with through-tapped holes passing from end to end. The holes are made to be congruent with corresponding drilled holes in the fork arms of the lower leg part intended to accommodate the lower leg tube and, in each case, are rigidly interconnected by means of fastening bolts. In the second possibility, the barrel may, on its ends, be provided with, in each case, one or several parallel ribs that can be passed through slots in the fork arms. Preferably, the fork arms are additionally provided with guide beads, which, in connection with a screw inserted into a central tapped hole of the barrel, aid in positioning or aligning the barrel.

On account of the mechanical stresses to which the barrel is exposed, it consists preferably of a steel part tempered to 60 Rockwell "C" hardness.

For the same reason, the clamping member should possess a correspondingly high degree of hardness or, according to a further development of the invention, be provided, within the area where it bears upon the barrel, with a replaceable steel part, preferably tempered at 60 Rockwell "C" hardness. For a better blocking of the movement and in order to have a larger braking area, the steel part is flattened within the area where it bears upon the barrel and, with a view to reducing the wear, the steel part is provided with a tempered clamping surface. The useful life of the clamping body or of the steel part can be extended by the steel part being adjustably supported in the clamping part. In a case of advanced wear, the steel part—perhaps a cylindrical roller—projects further from its mounting in the clamping member so that the requisite braking effect can be readjusted or reset. The clamping member itself consists preferably of titanium or titanium alloy.

In order to support a lifting action of the clamping member during the knee load relief phase or during the stretching or straightening movement, a pressure spring is disposed inside the knee joint casing which can be adjusted preferably in an indefinitely variable manner or to discrete, predeterminable values.

A further adjustment possibility or regulation is presented by a setscrew disposed within the casing, by which the free play between the barrel and the clamping member can be adjusted. This setscrew, too, can preferably be adjusted in an infinitely variable manner or to discrete, predetermined values.

Finally, the knee joint is also additionally provided with a fastening pin for the traction strap within the lower area of the knee joint casing between the barrel and the swivel axis. The pin preferably is arranged so as to be replaceable.

BRIEF DESCRIPTION OF THE DRAWINGS

In the following, the invention will be explained in detail with the aid of an embodiment depicted in the drawings.

DETAILED DESCRIPTION OF THE PREFERRED EMBODIMENT

Figure 1:
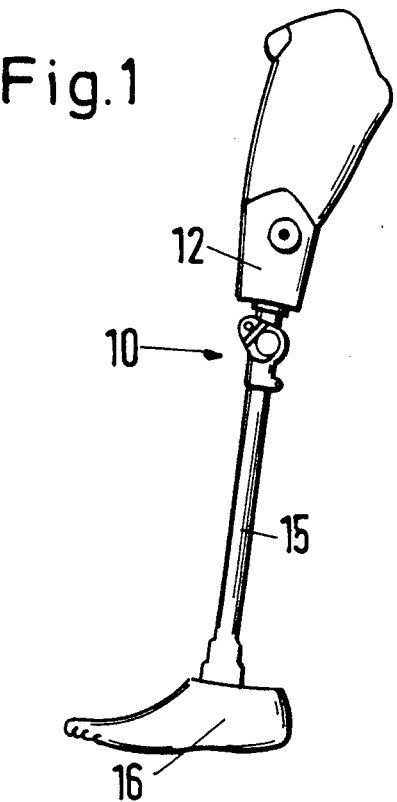
FIG. 1 shows, in a side elevation, a knee joint connected to a thigh shaft and a lower leg tube in the stretched or straightened position.
Figure 2:
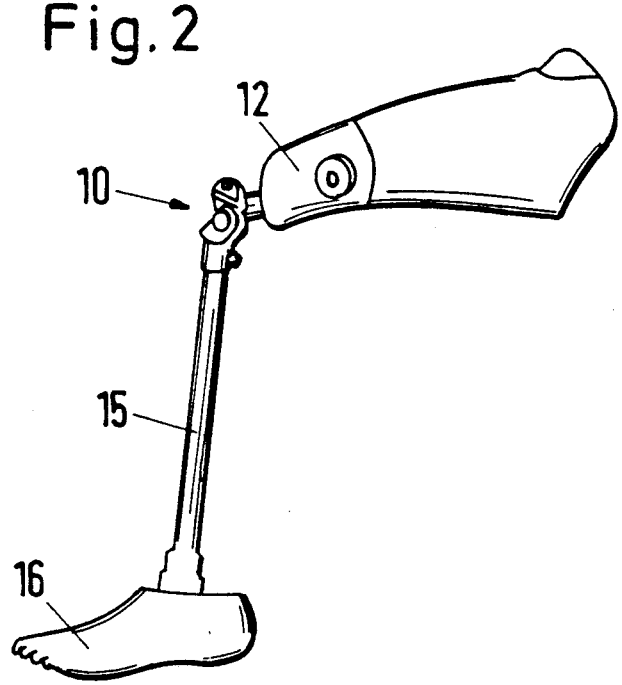
FIG. 2 shows, in a side elevation, the same arrangement in the bent position.
Figure 3:
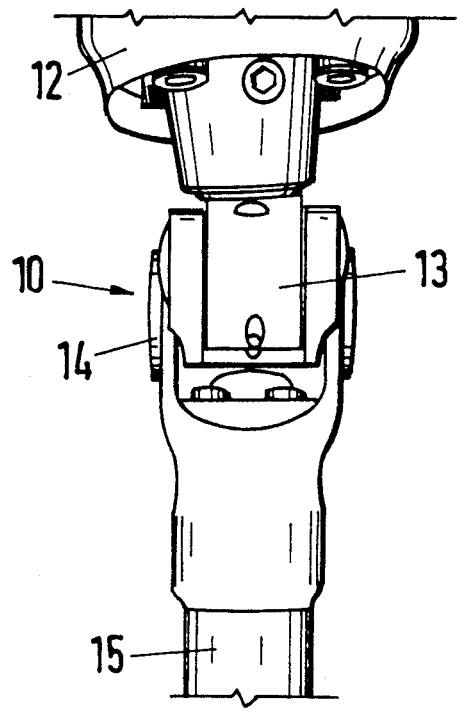
FIG. 3 shows, in a front view, an enlarged depiction of the knee joint in the stretched position.
Figure 4:
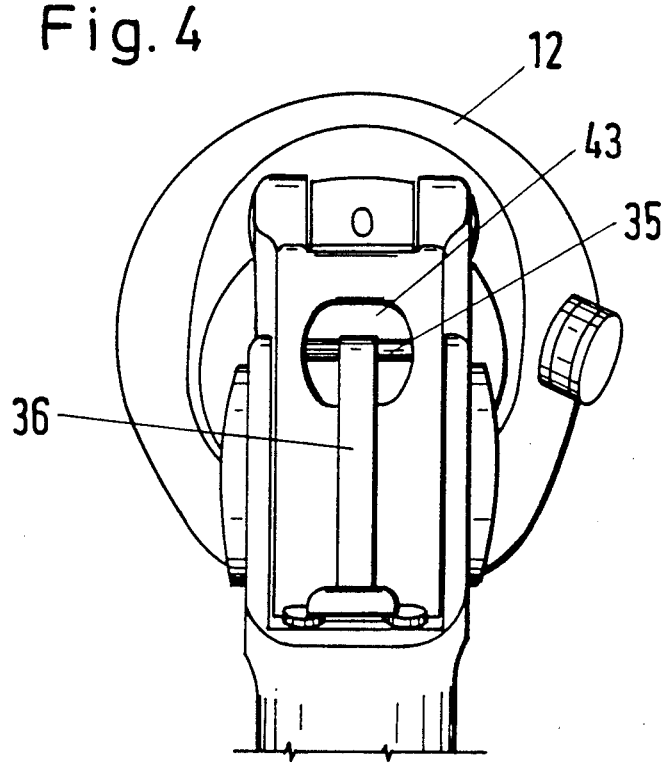
FIG. 4 shows the enlarged view per FIG. 3 in the bent position.
Figure 5:
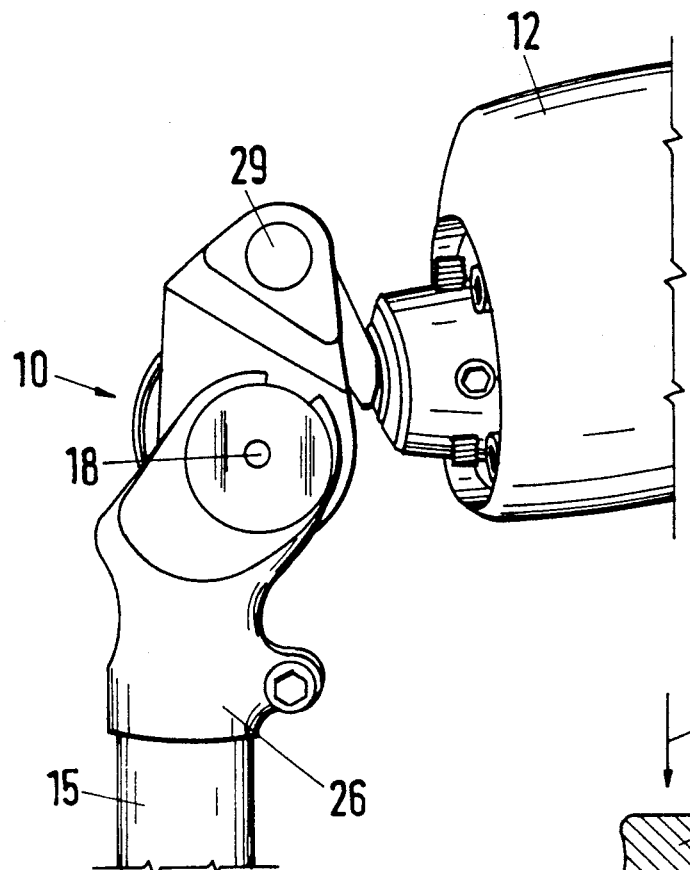
FIG. 5 shows, in a side elevation, an enlarged depiction of the knee joint in the bent position.
Figure 6:
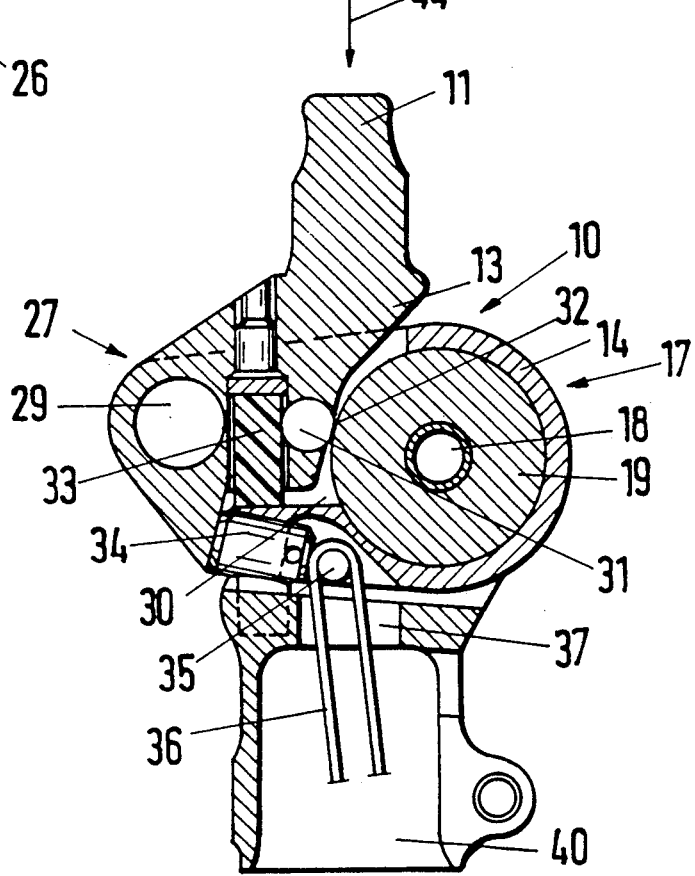
FIG. 6 shows a diagrammatical cross-sectional depiction of the knee joint according to the invention.
Figure 11:
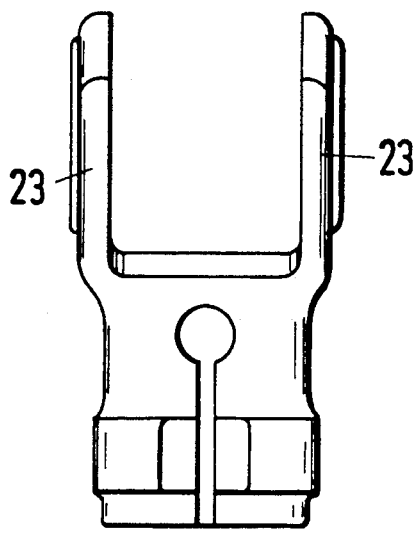
FIG. 11 shows a rear view of the lower leg part which is to accommodate the lower leg tube.
Figure 12:
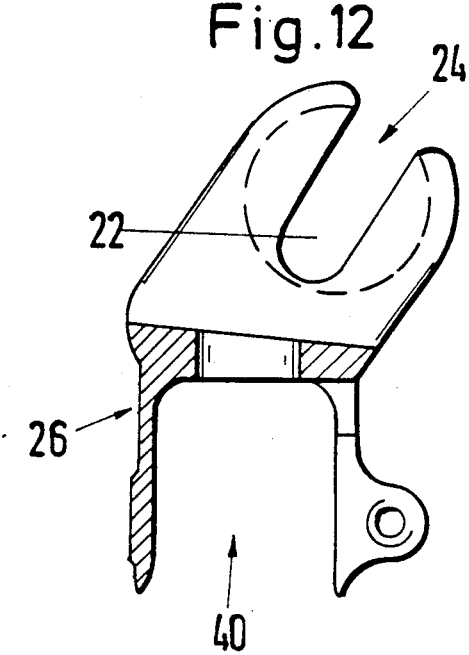
FIG. 12 shows, in a side elevation, the lower leg part.
Figure 13:
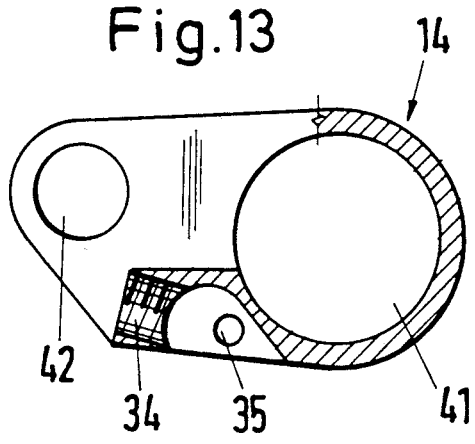
FIG. 13 shows, in a side elevation, the knee joint casing.

The artificial knee joint 10 shown in FIGS. 1-6 has a peg for attachment onto a thigh shaft 12, the peg 11 forming a part of the clamping member 13 shown in FIG. 6. The clamping member 13 is pivotingly mounted in a knee joint casing 14 while the lower leg tube 15 with an artificial foot attached at the end, is secured against rotation to a barrel 19 (FIG. 6) supported inside casing 14 by means of a lower leg part 26 having a fork arm 23 (FIGS. 11 and 12).

Figure 9:
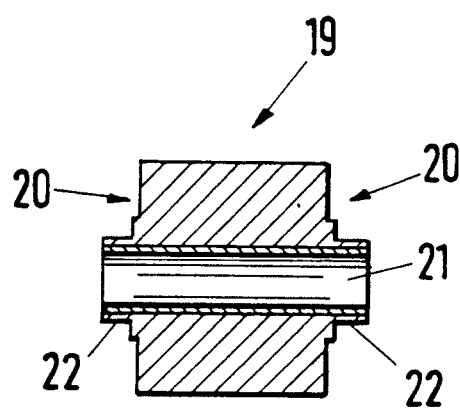
FIG. 9 shows a cross-sectional view of the barrel along the central axial plane.
Figure 10:
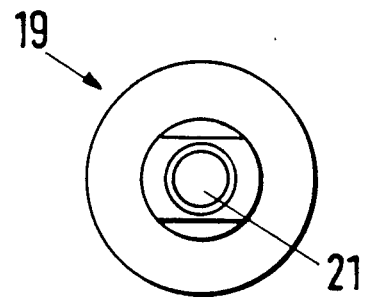
FIG. 10 shows a side view of the barrel.

As can be seen especially from FIG. 6, within the rear area of 17 of the knee joint 10 inside the knee joint casing 14, the barrel 19 is supported about a horizontal rotary axis 18, said barrel being depicted in the FIGS. 9 and 10. The ends 20 of the barrel 19 reveal a (in this case continuous) central tapped bore 21 for screwing the barrel 19 to the fork arms 23 of the lower leg part 26 depicted in the FIGS. 11 and 12 and intended to receive the lower leg tube. As indicated in FIGS. 9 and 10, each of the ends 20 of the barrel 19 is additionally provided with at least one parallel rib 22 which, in the fashion shown in FIG. 12, can be introduced into a slot 24 of each fork arm 23. The guide beads 25 of the fork arms 23 serve to position the fork arms with respect to the barrel 19 rigidly connected to the latter. A screw with as wide a flat head surface as possible, not shown in the drawing serves for fastening.

Figure 7:
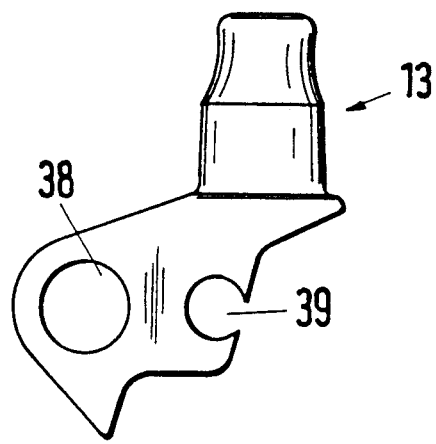
FIGS. 7 and 8 show opposite side elevations of the clamping member.
Figure 8:
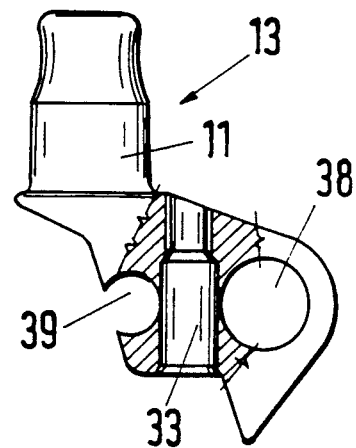
Figure 14:
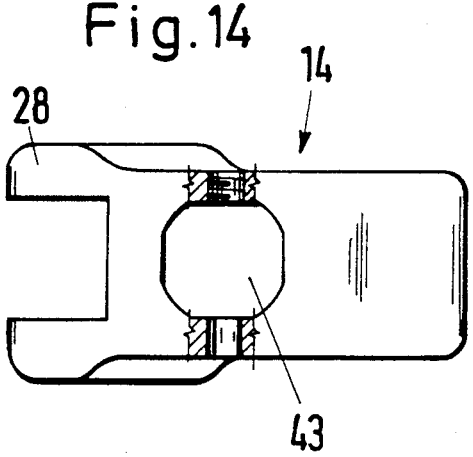
FIG. 14 shows the knee joint casing in a bottom plan view.
Figure 15:
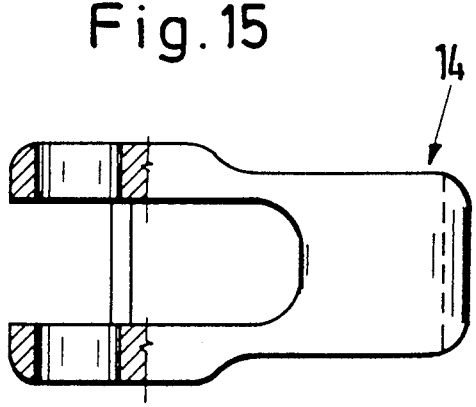
FIG. 15 shows the knee joint casing in a top plan view and FIG. 16 shows the knee joint casing as viewed from the front.
Figure 16:
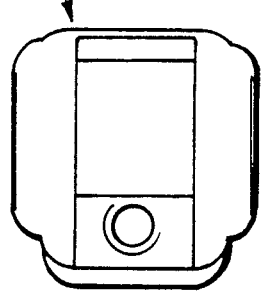

As shown in FIG. 6 within the front area 27, the casing 14 is provided with a forked mounting 28 (FIG. 14) for a swivel axis 29 of the clamping member 13. The swivel axis 29 consists of a bolt supported in the forked mounting 28 which penetrates a drilled hole 38 of the clamping member 13 (FIGS. 7 and 8). Within the area 30, in which the clamping member 13 and the barrel 19 finally come to bear against one another when a vertical load occurs, a steel part 31 is inserted into an aperture 39 of the clamping member 13. The steel part itself has a flattened and tempered clamping surface 32.

It is the function of the pressure spring 33 (FIGS. 6 and 8) to support the disengagement force of the knee joint in opposition to the weight load 44.

By means of a setscrew 34 accommodated inside the knee joint casing 14, it is possible to adjust the clamping member 13 so as to be infinitely variable in its position between the barrel 19 and the steel part 31. The fastening pin 35 of the traction strap 36 is horizontally secured within the lowe area 37 of the knee joint casing 14. The lower leg part 26 depicted in FIGS. 11 and 12 is, within its lower area, provided with a recess 40 for the accommodation or reception of the lower leg tube 15 with normal clamping means according to the state of the art. The traction strap 36 is secured in the lower leg part 26 or the leg tube 15 and produces a force to return the leg and knee joint to a straightened position.

The knee joint casing 14 is shown in greater detail in the FIGS. 13 thru 16. Especially within the rear area 17 (shown in FIG. 13 on the right-hand side) the casing has and almost closed recess 41 with a cylindrical internal surface for rotatably supporting the barrel 19. This recess is open only on the side which faces the clamping member 13 thus providing access in that region for the clamping member or the steel part 31 and the barrel 19 come to arrestingly bear against one another. The forked mounting 28 (FIG. 14) within the front area 27 (FIG. 13) has drilled holes 42 in both forks in which a bolt serving as a swivel axis for the clamping member 13 rests. The opening 43 within the lower area 37 of the casing 14 serves in particular for passing through the traction strap 36 which engages the fastening pin 35.

By means of the setscrew 34 within the knee joint according to the invention, the position of the clamping member 13 relative to the barrel 19 be adjusted under the force or load of the pressure spring 33 supporting the lifting action.

An essential element of the construction according to the invention is the positive rotationally fixed connection between the barrel 19 and the fork arm 23 or the lower leg part 26 that is to accommodate the lower leg tube 15. The fixed connection permits the barrel 19 to serve as a braking member in conjunction with the clamping member 13 and its support on the swivel axis 29. Each vertical load in excess of the preloading set in springs 33, see arrow 44 in FIG. 6, swivels the clamping member 13 in the casing 14 and the casing relative to the lower leg part 26 and the barrel 19 so that the steel part 31 comes to bear upon the barrel and constrains pivotal movements of the knee joint. All extension movements of the knee joint are maintained hereby, i.e. without any impairment of the stretching or straightening movement of the prosthesis. An unintentional buckling is no longer possible.

We claim:

1. An artificial knee joint for a patient comprising:
  a clamping member having an attachment for a thigh shaft;
  a knee joint casing pivotally connected with the clamping member at a swivel axis extending generally horizontally when the patient is walking, a leg part accommodating a lower leg tube of a leg prosthesis and connected with the knee joint casing at a rotary axis extending generally parallel to the swivel axis to provide for pivotal movement of the knee joint;

an essentially cylindrical barrel rotationally fixed with the leg part coaxially of the rotary axis of the leg part and knee joint casing for pivotal movements of the barrel together with the leg part relative to the knee joint casing, the cylindrical barrel being disposed within the casing in close proximity to the clamping member so as to permit the clamping member to bear upon the cylindrical surface of the barrel and brake the pivotal movements of the knee joint; and load responsive means interposed between the clamping member, and the leg part to maintain up to a predetermined load the clamping member and the cylindrical barrel within the knee joint casing in non-bearing relationship in opposition to the patient's weight for free pivotal movements of the joint, the load responsive means otherwise being responsive to weight applied by the patient to the joint to bring the clamping member and the cylindrical surface of the barrel into bearing relationship to brake the pivotal movements of the knee joint.

2. Knee joint according to claim 1 characterized in that the barrel is a steel part tempered to 60 Rockwell "C" hardness.

3. Knee joint according to claim 1, characterized in that the clamping member, within the area where it bears upon the barrel, is provided with a replaceable steel part.

4. Knee joint according to claim 3, characterized in that the steel part is flattened within the area where it bears upon the barrel and is provided with a tempered clamping surface.

5. Knee joint according to claim 3, characterized in that the steel part is adjustably supported in the clamping member.

6. Knee joint according to claim 3, characterized in that the clamping member consists of titanium or titanium alloy.

7. Knee joint according to claim 1, characterized in that the knee joint casing is provided with a setscrew for adjusting or regulating the play between the barrel and the clamping member.

8. Knee joint according to claim 7, characterized in that the setscrew is adjustable so as to be continuously variable or discretely variable.

9. A knee joint according to claim 1 characterized in that the leg part and the barrel are rotationally fixed to one another by bolting.

10. A knee joint according to claim 1 characterized in that the leg part has a forked end, and the barrel has parallel ribs engaged in the forked end of the leg part to fix the barrel and leg part rotationally to one another.

11. A knee joint according to claim 1 characterized in that a traction strap extends between the knee joint casing and the leg part for straightening the knee joint, and the traction strap is mounted by means of a removable fastening pin in a lower area of the casing between the barrel and the swivel axis for interchangability of the traction strap.

* * * * *